US008676598B2

(12) United States Patent
Kuriyan

(10) Patent No.: US 8,676,598 B2
(45) Date of Patent: Mar. 18, 2014

(54) CHRONIC POPULATION BASED COST MODEL TO COMPARE EFFECTIVENESS OF PREVENTIVE CARE PROGRAMS

(76) Inventor: Jacob George Kuriyan, Corrales, NM (US)

(*) Notice: Subject to any disclaimer, the term of this patent is extended or adjusted under 35 U.S.C. 154(b) by 159 days.

(21) Appl. No.: 12/798,083

(22) Filed: Mar. 29, 2010

(65) Prior Publication Data

US 2010/0250277 A1    Sep. 30, 2010

Related U.S. Application Data

(60) Provisional application No. 61/164,929, filed on Mar. 31, 2009.

(51) Int. Cl.
*G06Q 50/22*    (2012.01)
*G06Q 40/08*    (2012.01)

(52) U.S. Cl.
USPC .................................................. 705/2; 705/4

(58) Field of Classification Search
USPC ................... 705/2–4; 707/1, 5; 600/300, 324
See application file for complete search history.

(56) References Cited

U.S. PATENT DOCUMENTS

| | | | | |
|---|---|---|---|---|
| 7,213,009 | B2 * | 5/2007 | Pestotnik et al. | 706/46 |
| 7,392,201 | B1 * | 6/2008 | Binns et al. | 705/4 |
| 7,685,000 | B1 * | 3/2010 | Petit et al. | 705/2 |
| 2002/0013515 | A1 * | 1/2002 | Iliff | 600/300 |
| 2002/0038227 | A1 * | 3/2002 | Fey et al. | 705/3 |
| 2002/0099686 | A1 * | 7/2002 | Schwartz et al. | 707/1 |
| 2003/0060688 | A1 * | 3/2003 | Ciarniello et al. | 600/300 |
| 2003/0130973 | A1 * | 7/2003 | Sumner et al. | 706/45 |
| 2005/0091083 | A1 * | 4/2005 | McGuigan et al. | 705/3 |
| 2005/0240434 | A1 * | 10/2005 | Wooten et al. | 705/2 |
| 2005/0267338 | A1 * | 12/2005 | Lipman | 600/300 |
| 2006/0154210 | A1 * | 7/2006 | Martin et al. | 433/215 |
| 2006/0287888 | A1 * | 12/2006 | Averill et al. | 705/2 |
| 2008/0146334 | A1 * | 6/2008 | Kil | 463/36 |
| 2008/0201174 | A1 * | 8/2008 | Ramasubramanian et al. | 705/3 |
| 2008/0221419 | A1 * | 9/2008 | Furman | 600/324 |
| 2008/0275729 | A1 * | 11/2008 | Taggart et al. | 705/2 |
| 2009/0138285 | A1 * | 5/2009 | Denberg | 705/3 |
| 2009/0216747 | A1 * | 8/2009 | Li et al. | 707/5 |
| 2011/0264378 | A1 * | 10/2011 | Breton et al. | 702/19 |
| 2012/0303381 | A1 * | 11/2012 | Bessette | 705/2 |

OTHER PUBLICATIONS

A Randomized, Placebo-Controlled, Clinical Trial of High-Dose Supplementation With Vitamins C and E, Beta Carotene, and Zinc for Age-Related Macular Degeneration and Vision Loss: AREDS Report No. 8. Arch Ophthalmol. 2001;119(10):1417-1436. (Retr Internet Apr. 13, 2013). URL:<http://www.ncbi.nlm.nih.gov/pmc/articles/PMC1462955/pdf/nihms9674.pdf>.*

* cited by examiner

*Primary Examiner* — Lena Najarian
*Assistant Examiner* — Natalie A Pass
(74) *Attorney, Agent, or Firm* — Moazzam & Associates, LLC

(57) ABSTRACT

Our invention is a cost model for healthcare, based not on "age", as it is done currently, but on "chronic illness" as a risk factor. Using the model it is possible to derive two burden numbers, "Primary" and "Secondary" that is an inverse measure of the success of primary and secondary preventive care programs. Using this new metric, a better explanation for cost increases is possible. It can help estimate increases more accurately and make explicit suggestions on where the focus of attention should be to lowering costs. Trend lines of the metric can measure performance of care programs month by month and not have to wait a decade to yield perceptible results.

A particular embodiment of this model is the software program described in this application, called Health Keys, which serves as a decision support system for CFOs of companies and health plans to help institute relevant preventive care programs and measure the success of them. Health Keys is one example of a "useful, concrete and tangible result" that is based on our invention of a new cost model.

17 Claims, 9 Drawing Sheets

Sample Transition Matrix Elements for July '07 & Associated Costs

Legend: NC- non chronic; H – Heart; D – Diabetes; HC – Hyper-cholesterol; HT – Hypertension; O – Obesity; A – Asthma; OA – Osteoarthritis; 2D – Two of the earlier chronic diseases; 3 D – Three chronic diseases; >3D – more than three chronic diseases; C – cancer.

Fig. 1 Patient Transitions in Time (See "Static Component")
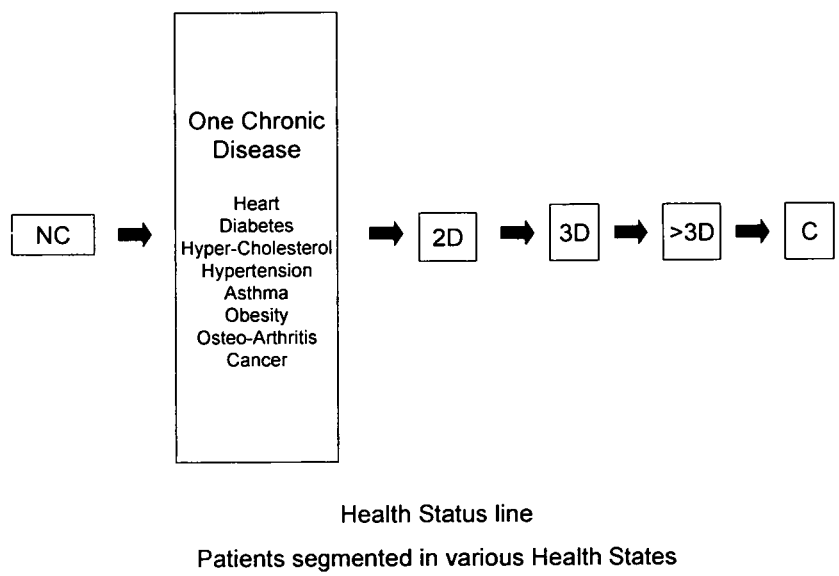
Health Status line
Patients segmented in various Health States

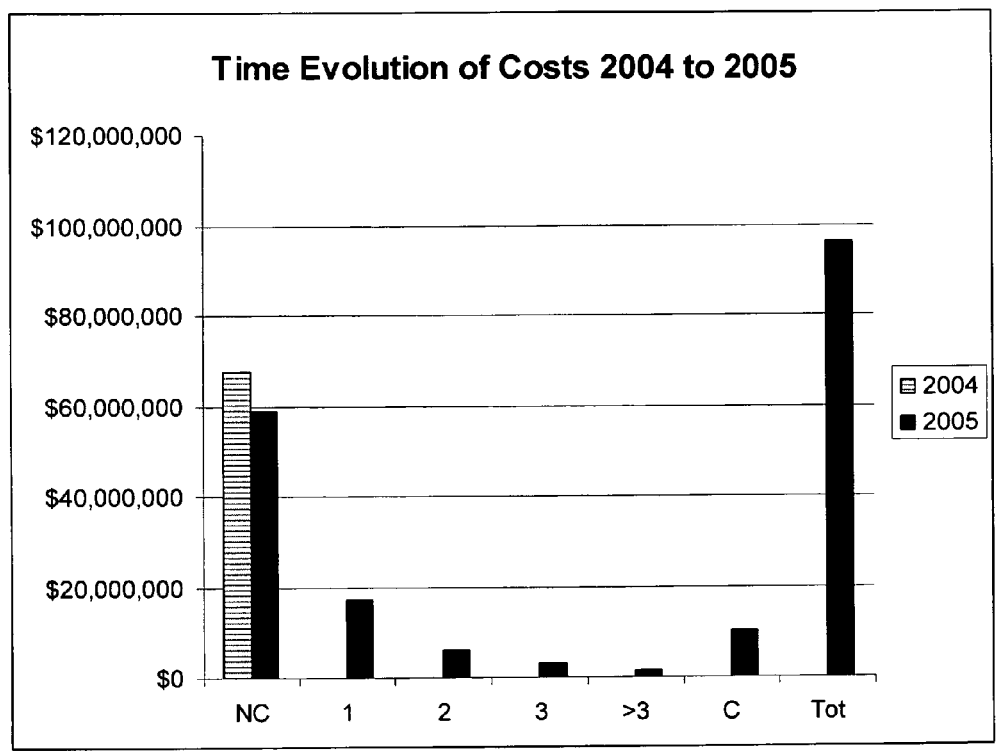
Fig 2. Cost increase for 2004 non-chronic patients in one year

Fig. 3 Flow diagram for identifying patients with diabetes (Implementation Step #1)
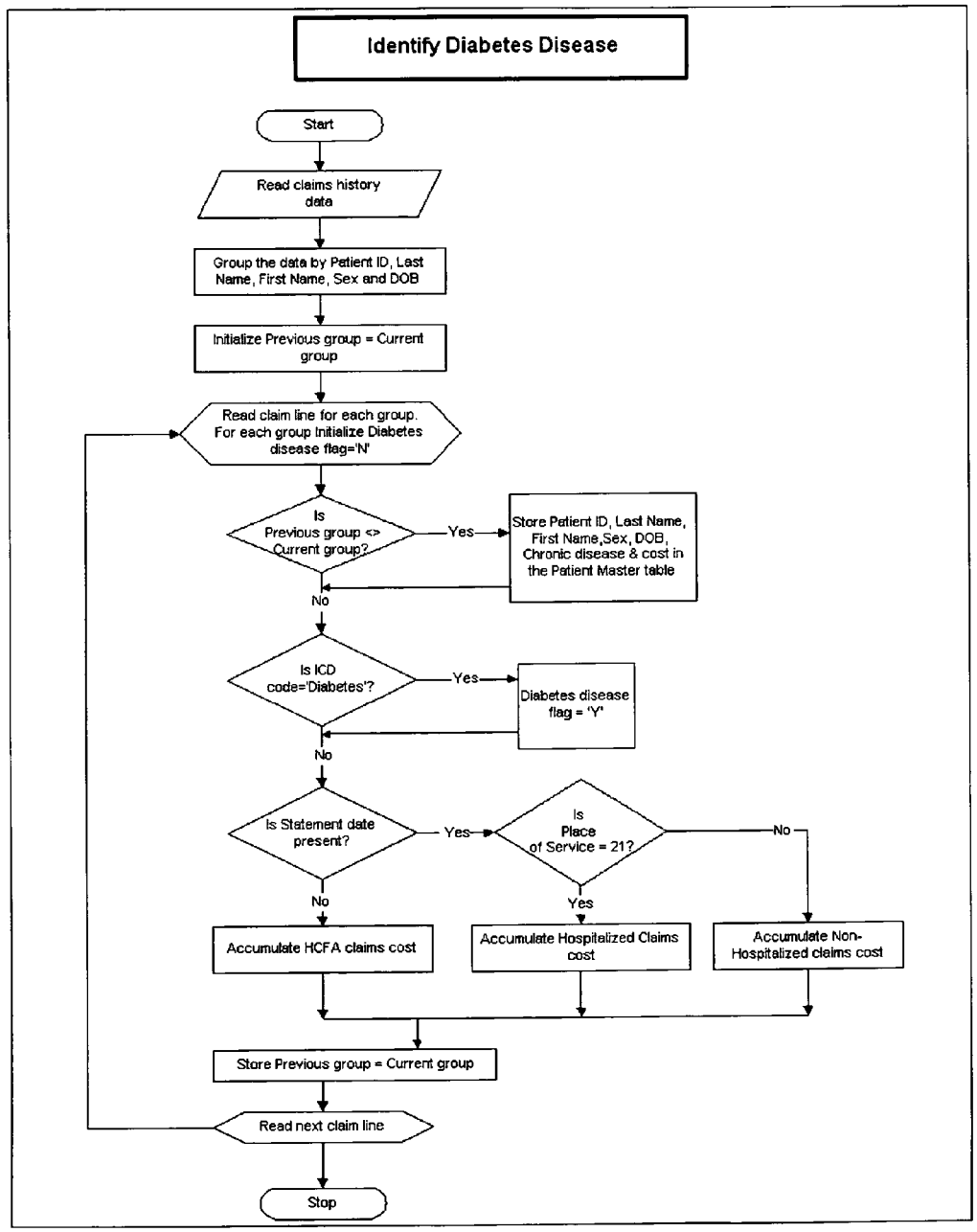

Fig. 4 Flow Diagram depicting patient transitions
(Implementation Step #3):
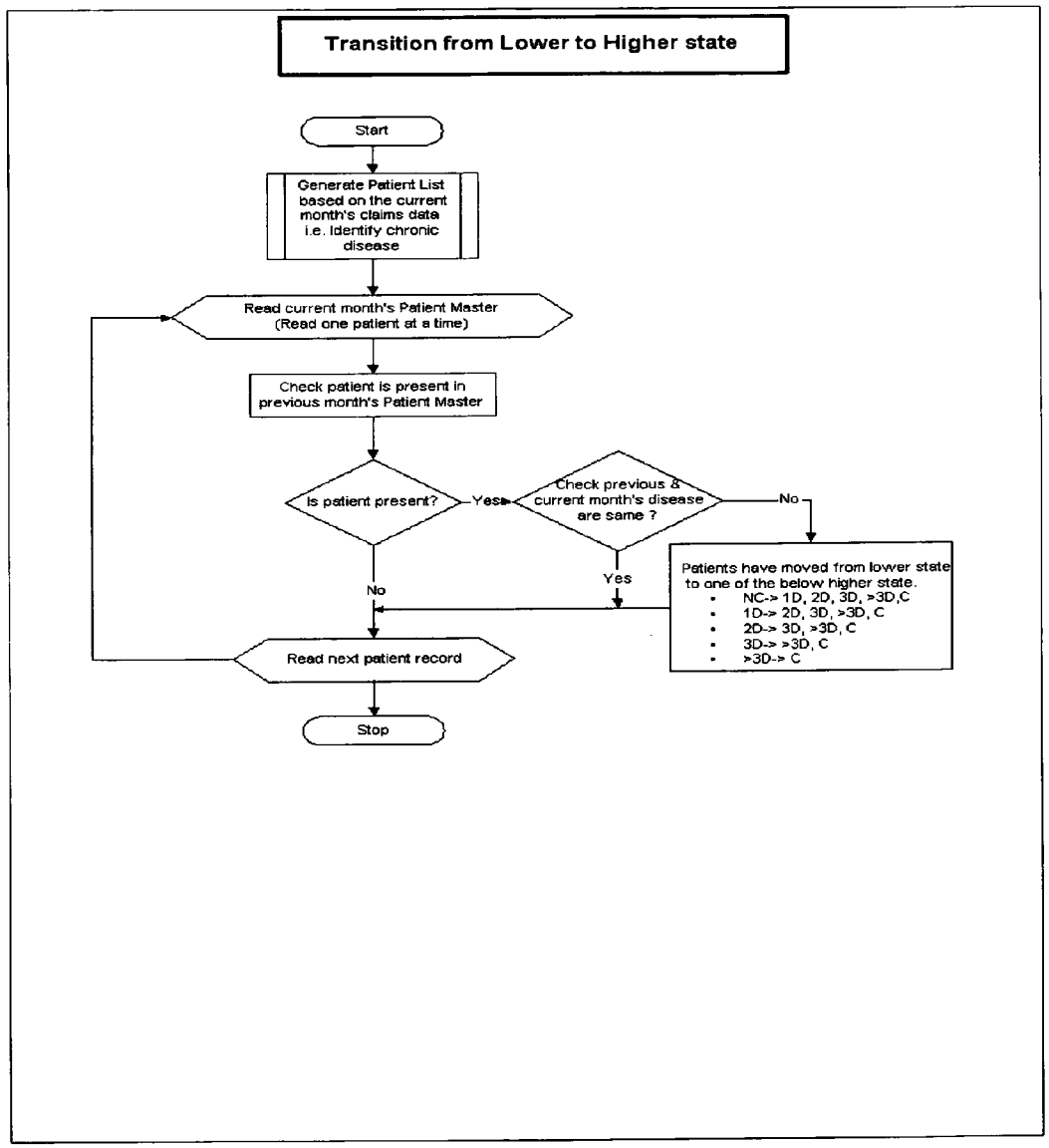

Fig. 5 Flow diagram depicting setting goals
(Implementation Step #4)
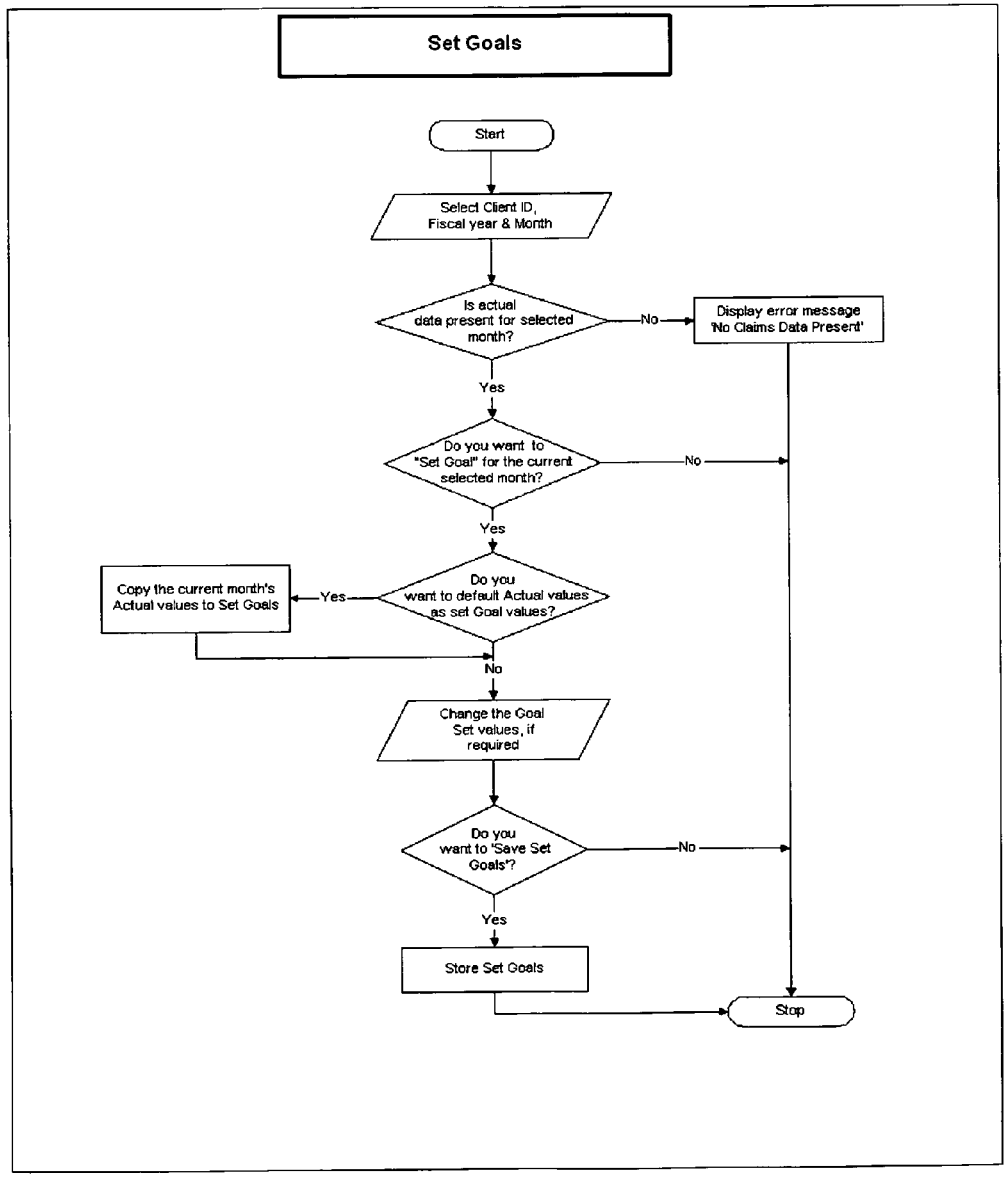

Fig. 6 Flow diagram of trend analysis – Compare with selected goal
(Implementation Step #6)
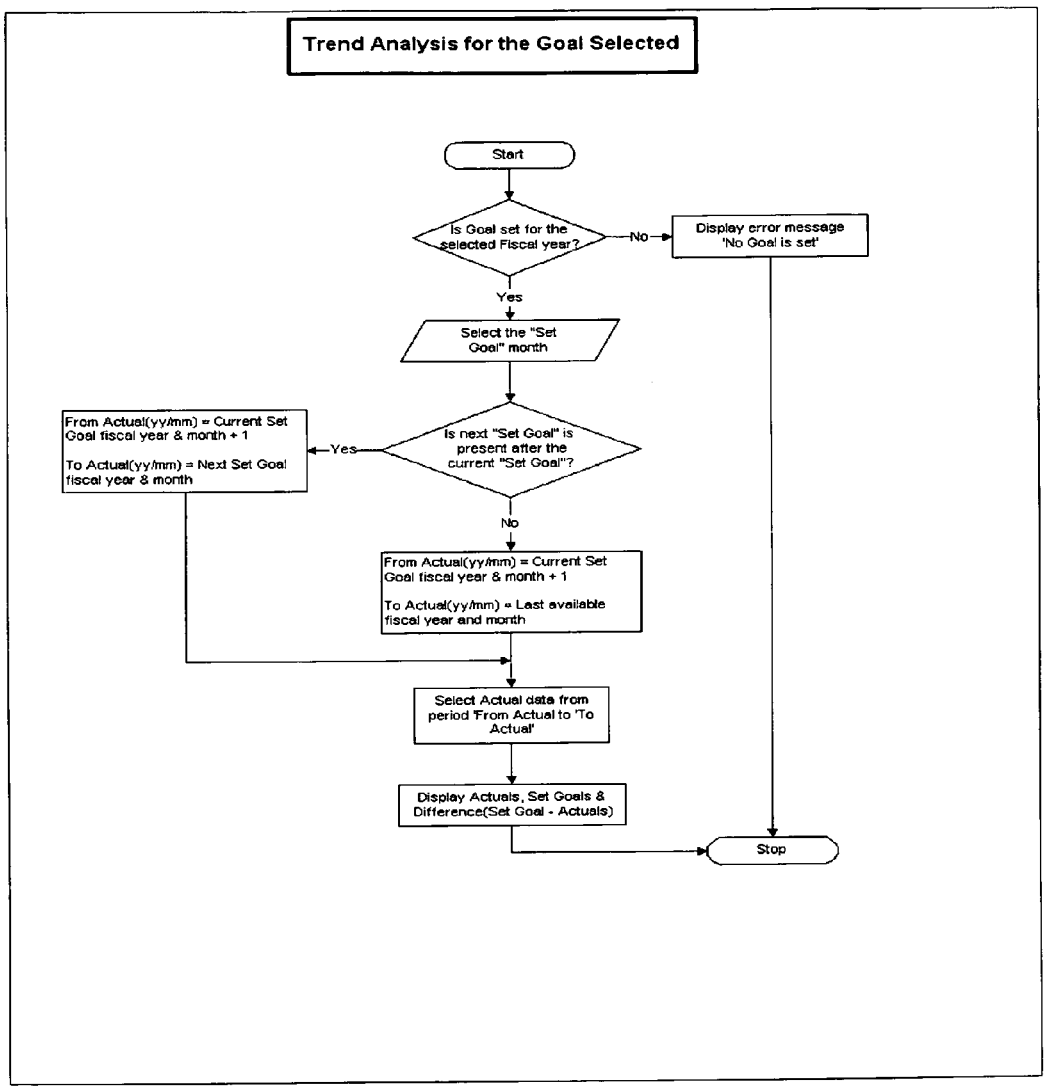

Fig. 7. Sample Transition Matrix Elements for July '07 & Associated Costs

|  | Jul 07 |  |  |  |  |  |  |  |  |  |  |  |  |
|---|---|---|---|---|---|---|---|---|---|---|---|---|---|
| Row or Col # | Col 1 | Col 2 | Col 3 | Col 4 | Col 5 | Col 6 | Col 7 | Col 8 | Col 9 | Col 10 | Col 11 | Col 12 | Col 13 |
| Row 1 | Cost=> | $165 | $972 | $472 | $284 | $321 | $260 | $281 | $350 | $446 | $580 | $909 | $865 |
| Row 2 | Disease | NC | H | D | HC | HT | O | A | OA | 2D | 3D | >3D | C |
| Row 3 | NC | -883 | 14 | 43 | 173 | 199 | 69 | 76 | 62 | 98 | 24 | 2 | 123 |
| Row 4 | H |  | -10 |  |  |  |  |  |  | 9 | 1 | 0 | 0 |
| Row 5 | D |  |  | -39 |  |  |  |  |  | 31 | 5 | 0 | 3 |
| Row 6 | HC |  |  |  | -139 |  |  |  |  | 107 | 7 | 3 | 22 |
| Row 7 | HT |  |  |  |  | -198 |  |  |  | 157 | 14 | 0 | 27 |
| Row 8 | O |  |  |  |  |  | -29 |  |  | 20 | 4 | 0 | 5 |
| Row 9 | A |  |  |  |  |  |  | -58 |  | 46 | 3 | 0 | 9 |
| Row 10 | OA |  |  |  |  |  |  |  | -46 | 37 | 1 | 1 | 7 |
| Row 11 | 2D |  |  |  |  |  |  |  |  | -335 | 236 | 21 | 78 |
| Row 12 | 3D |  |  |  |  |  |  |  |  |  | -269 | 223 | 46 |
| Row 13 | >3D |  |  |  |  |  |  |  |  |  |  | -68 | 68 |
| Row 14 | C |  |  |  |  |  |  |  |  |  |  |  |  |
| Row 15 | Net Change | -883 | 4 | 4 | 34 | 1 | 40 | 18 | 16 | 170 | 26 | 182 | 388 |

Legend: NC- non chronic; H – Heart; D – Diabetes; HC – Hyper-cholesterol; HT – Hypertension; O – Obesity; A – Asthma; OA – Osteoarthritis; 2D – Two of the earlier chronic diseases; 3 D – Three chronic diseases; >3D – more than three chronic diseases; C – cancer.

Every row stands for a particular disease state defined as the "From Disease state" and every column after the first is the "To Disease state"
Fig.8 Sample Chronic Care Map™ of Arkansas using simulated data, as part of a Preventive Care Atlas™ of the US
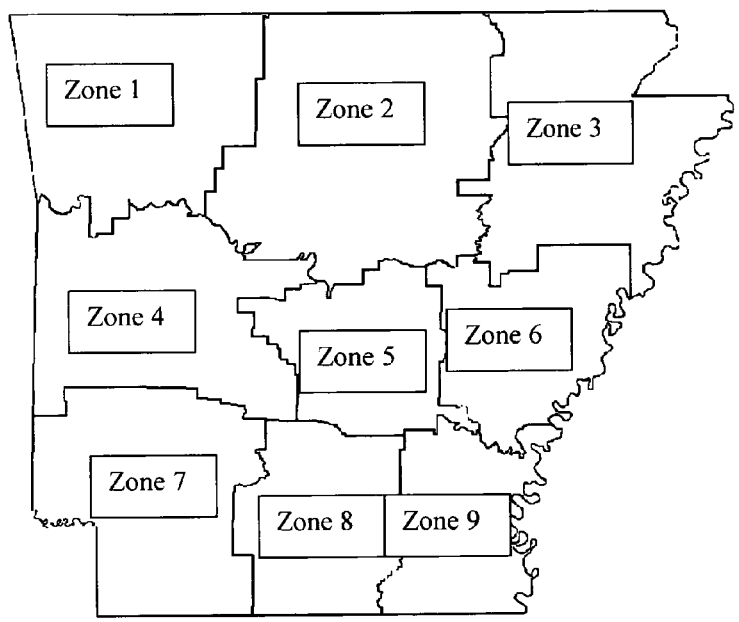
| Zone   | 1        | 2        | 3        | 4        |
|--------|----------|----------|----------|----------|
| PB     | 79       | 95       | 84       | 94       |
| SB     | 158      | 163      | 176      | 171      |
| PB$$   | $17,909  | $3,857   | $17,640  | $16,923  |
| SB $$  | $28,891  | $32,004  | $39,783  | $40,816  |
| Zone   | 5        | 6        | 7        | 8        | 9        |
|--------|----------|----------|----------|----------|----------|
| PB     | 107      | 101      | 92       | 121      | 133      |
| SB     | 150      | 188      | 181      | 174      | 149      |
| PB$$   | $20,068  | $23,462  | $16,928  | $42,752  | $17,099  |
| SB $$  | $26,250  | $42,076  | $37,675  | $36,822  | $31,511  |

Fig. 9. Sample of Care & Cost Scatter Plot for Zones
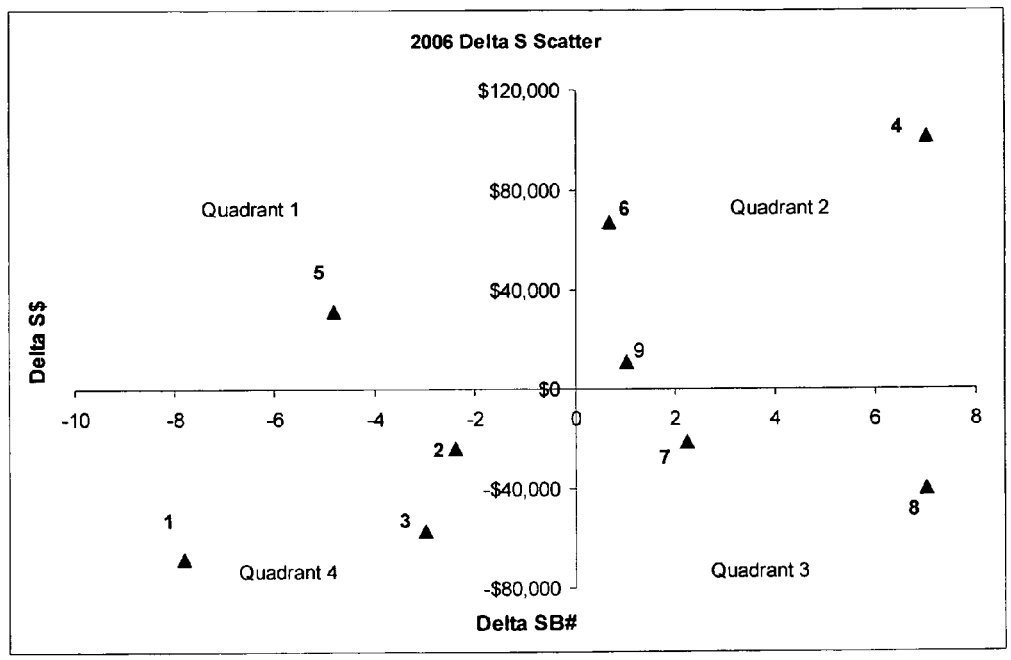
Note:
Delta SB# refers to the quantity (SB# - Average SB#)
Delta S$ refers to the quantity (S$ - Average S$)
The black triangles refer to the various values of Delta SB# and Delta S$ for the zones numbered 1 through 9. Zone numbers are placed next to the triangle icons.

CHRONIC POPULATION BASED COST MODEL TO COMPARE EFFECTIVENESS OF PREVENTIVE CARE PROGRAMS

CROSS-REFERENCES TO RELATED APPLICATIONS

The application claims the priority of U.S. Provisional Application Ser. No. 61164929 entitled "A cost model for US Healthcare based on a chronic population based delivery system" filed on 31 Mar. 2009, the entire contents and substance of which are hereby incorporated in total by reference.

SEQUENCE LISTING

Not applicable.

STATEMENT REGARDING FEDERALLY SPONSORED RESEARCH OR DEVELOPMENT

Not applicable.
The Names of the Parties to a Joint Research Agreement
Not applicable.
Reference to a Sequence Listing, a Table or Computer Program
Not applicable.

BACKGROUND OF THE INVENTION (1) Field of the Invention

This invention relates to a method of comparing the effectiveness of preventive care programs for chronic patients using a metric for performance that can then be illustrated via the use of a "Preventive Care Atlas™" and scatter plots of care performance and Costs. More specifically this invention relates to the creation of a new cost model for a population, with chronic disease as the designated risk, so as to calculate trends in incidence, prevalence and severity of chronic conditions in a population and estimate the associated impact on healthcare costs.

(2) Description of Related Art

General description of the historical problem: Healthcare costs have been rising, mostly because more people have become chronically ill, and there is an increasing realization that until we can lower medical needs by keeping people healthy the trend will continue unabated. There is also the fear that preventive care programs designed to keep chronic people healthy can be expensive and employers need to see a return on their investment before financial managers in businesses will offer their unreserved support. But to identify the beneficial effects of a preventive care program on an individual may take many years and employers are reluctant to invest today for what can only become visible many years hence. Clearly what is needed is a method to help employers measure cost and savings arising from preventive care programs.

Businesses use models as laboratories. Pricing models can be used to understand market forces of demand and supply. Cost models help companies budget their resources and manage costs. Without good models businesses will find themselves financially adrift using trial and error instead of getting actionable guidance from models.

Healthcare is no exception in the use of models to guide business decisions and there are many popular examples. Analysis of prior claims data is used to model utilization and negotiate favorable payment rates to specialists and labs. HMOs used the concept of "prepaid" models to transfer their risk to primary care physicians. To bring uniformity to treatment Medicare has used a DRG (Diagnosis Related Group) model to bundle hospital services and healthplans have paid based on models defining "episodes of care" rather than for individual office visits and procedures.

But the basic cost model in healthcare was designed for underwriting insurance premiums and actuaries used the same risk factors that life insurers have used—age and sex of an individual. Two or more decades ago it was possible to explain annual rising costs as being due to the aging of the employee population, the assumption being older people have more medical needs and so incur more costs. But that is not the case any more.

There are two problems with using age and sex to explain rising costs in a population. First, claims data from sample populations clearly establishes that aging cannot be the sole reason because annual cost increases appear in many age segments not just in the oldest ones. Second, this is giving rise to a negative psychological effect that is hurting reform efforts in the market. If rise in costs are due to the natural process of aging, as it is argued, then, short of rejuvenation, there is nothing much that can be done. This results in financial managers of companies being helplessly sidelined as they watch annual healthcare costs rise unabated.

That is not to say that actuaries have not recognized the need for taking into account the chronic illness of an enrollee in determining premiums. In fact current cost models assign a statistical probability for acquiring a chronic illness or developing complications and it is part of a "burden" associated with the person. But to get the results for a population it will then be necessary to multiply the various individual probabilities and thus introduce a very large number of adjustable variables. This challenges "parsimony", i.e., using the least number of variables, rendering many of the predictions for populations of questionable value.

To put it another way, there is not a "cost model" that adequately accounts and measures the temporal development of disease and costs of a population. Without such measurements, comparisons are not quantitative but qualitative, and judgment of effectiveness and performance of preventive care programs remain vague.

BRIEF SUMMARY OF THE INVENTION

Briefly described, the invention comprises of a new cost model with the following features:

- The patient population is divided into segments (or health states) defined by chronic illness of increasing severity.
- Segments (or health states) are ordered in increasing severity as those patients with: no chronic conditions, one chronic condition, two chronic conditions, three chronic conditions or more chronic conditions.
- Each patient is assigned uniquely to one of these segments (or health states).
- Because chronic illness has no cure, passage of time in the model is represented by patients in one health state staying put or transitioning to another health state that represents a more severe chronic condition and incurring greater costs.
- The role of preventive care programs is to prevent patients from moving to a health state with more severity and costs.
- The number of patient transitions from one health state to another is an inverse measure of the success of a corresponding preventive care program and these numbers, defined as "Primary Burden" and "Secondary Burden", and the associated costs of transitions can be used to compare effectiveness of different care programs and interventions.

By plotting the values of the burden numbers and associated costs on a geographical map (FIG. 8) it is then possible to create a Preventive Care Atlas™.

An alternate visualization of the comparison is through a scatter plot (FIG. 9) of burden numbers and associated costs, when the most efficient programs will fall into a single quadrant.

It turns out that prior cost models based on statistical assumptions and using age as a risk factor worked well about two decades ago. When the future is a repetition of the past, then statistical models are expected to work very well as predictors. But the spread and prevalence of chronic illness and cancer have distorted the medical needs of populations beyond the limits of statistical extrapolations. In analyzing the medical claims data of an employee population it became obvious that it wasn't aging that caused the rise in medical needs but aging in an unhealthy fashion. In other words, many employees became chronically ill with diseases like hypertension and diabetes and at an early stage these diseases tend to get neglected because there is no pain nor any overt signs of problems. In time the disease festers, causing many complications and they are mistakenly attributed to aging.

Our goal was to create a new cost model that uses a risk factor different from "age". Because of the prevalence and rise of chronic illness nationwide it made sense to build a cost model based on chronic disease as the new risk factor instead of age, and use the time evolution of chronic populations to explain the temporal increase in healthcare costs This invention solves multiple problems in healthcare. The primary one has to do with the inability of current healthcare cost models to predict next year's costs accurately based solely on statistical factors. Healthplans (especially their under-writing departments) and self-insured companies will benefit from the more accurate estimates of costs resulting from the new model because chronic patients have predictable medical needs and costs. In other words, while the model does not predict which enrollees will develop a chronic condition or complications, once identified by the diagnosis code in the claim as belonging to a specific health state then the annual medical cost for the new health state is known.

Knowing the chronic illness of the population makes it easy to target the specific diseases of interest. These are chronic diseases and by definition they have no cure. For those chronic patients preventive care is the only option available. Without adequate chronic care, the health states of enrollees tend to worsen with time and costs increase. So doing nothing is a guarantee for higher future costs and healthcare delivered must guard against these rising costs. Therefore, as a result of the new model, preventive care programs become an integral part of the healthcare purchase made by companies.

As we describe the details of the invention the following will become apparent as well:

The new cost model provides actionable insights into the effective means for lowering costs It is possible to measure the success or failure of a preventive care program quantitatively using Primary and Secondary Burdens and compare the efficacy of preventive care programs. Employers can use the measure to deduce if the preventive care programs are working or not.

Computer programs can be built based on the model to solve a variety of healthcare management problems.

BRIEF DESCRIPTION OF THE DRAWINGS

FIG. 1 Patient Transitions in Time (See "Static Component")

Explanatory note to FIG. 1.:

This is referred to in the section entitled "Description of the Invention" as Static Component. The population is divided into various health segments, Non Chronic, 1 Disease, 2 Disease etc. and arranged from left to right. This figure then describes the typical temporal development of a population, from left to right. For example, non-chronic patients, over a period of time can develop one or more chronic diseases, and move to the right in the figure, to any of the health segments. Because there is no cure for chronic disease, the re is never a movement from right to left in the figure. Also, transitions to "C" (cancer) are allowed from any of the states defined in FIG. 1 above. As stated in the text, cancer costs are so large that it belongs in a special category.

FIG. 2. Cost increase for 2004 non-chronic patients in one year

Explanatory note to FIG. 2:

In this example, about 55,000 non chronic patients in 2004 incurred costs of about $67.5 million. During the following year, many non chronic patients remained in the same health segment and they cost about $60 million. But many others acquired one or more chronic diseases in 2005—it cost about $18 million for those with single chronic disease; $8 million for those with two chronic diseases etc. In all, the same population that cost $67.5 million in 2004 cost $97.2 million in 2005. This then is the transition costs for a patient population.

FIG. 3 Flow diagram for identifying patients with diabetes

Explanatory note for FIG. 3.

This is described in Implementation Step #1 in "Details of the Invention" and shows the logic used to identify diabetes patients. Other patients with chronic & cancer diseases are similarly identified from Claims data.

FIG. 4 Flow Diagram depicting patient transitions

Explanatory note for FIG. 4.

This is described in Implementation Step #3 in "Details of the Invention" and describes the logic used in the identification of patient transitions.

FIG. 5 Flow diagram depicting setting goals

Explanatory Note for FIG. 5.

This flow chart describes Implementation Step # 4 in "Details of the Invention" and shows the logic used in setting goals.

FIG. 6 Flow diagram of trend analysis—Compare with selected goal

Explanatory note for FIG. 6:

See Implementation Step #6 in "Details of the Invention" for a description of this work flow. This flow chart describes the logic used to compare trend lines with the goals set.

FIG. 7 A typical example of a Transition matrix

Explanatory Note for FIG. 7. This transition matrix for the period July '07 shows how many patients have moved from one health state (described in the rows of the first column as NC, H,D,HC,HT,O,A, OA, 2D, 3D, >3D) to another health state defined in the columns with the same notation, NC, H, D, etc. The legend for the nomenclature used is: NC—non chronic; H—Heart; D—Diabetes; HC—Hyper-cholesterol; HT—Hypertension; O—Obesity; A—Asthma; OA—Osteoarthritis; 2D—Two of the earlier chronic diseases; 3 D—Three chronic diseases; >3D—more than three chronic diseases; C—cancer FIG. 8. Sample of a Preventive Care Map of Arkansas divided into zones Explanatory Note for FIG. 8. This is a sample map created using simulated data. State of AR is divided into 9 arbitrary zones and for each zone we have Primary Burden (PB#) and associated Primary Burden cost (PB$$) and Secondary Burden (SB#) and associated Secondary Burden Cost (SB$$).

FIG. 9. Sample of Care and Cost Scatter Plot

Explanatory Note for FIG. 9. This uses a scatter plot to display Secondary Burden and Secondary Burden Cost, with the origin defined as the Average value of Secondary Burden and Secondary Burden Cost. The "best" quadrant is #3 while the "worst" is Quadrant 2.

Delta SB# refers to the quantity (SB#-Average SB#)

Delta S$ refers to the quantity (S$-Average S$)

The dots refer to the various values of Delta SB# and Delta S$ for the 9 zones.

DETAILED DESCRIPTION OF THE INVENTION

The cost model has a "static" description of the population and a dynamic component that describes the time evolution of the population.

Static component: In this new cost model the patient population is segmented according to "risk" defined by chronic illness, and listed, left to right, in hierarchical order of increasing severity and, therefore, cost, as follows: no chronic disease, one chronic disease, two chronic diseases, three chronic disease and ">3" chronic diseases. (See FIG. 1)

Diagnosis codes appearing in prior medical claims are used to classify patients into these various risk categories or "health states." In paper medical claims as well as the HIPAA electronic versions, diagnosis codes are usually expressed as ICD-9 or DRG codes. Diabetes, heart disease, asthma, hypertension and hyper-cholesterol are the most frequently occurring chronic diseases. Depending on the sample population, other chronic diseases may be added.

Prior medical and pharma claims can also be analyzed to obtain an average cost of treatment for each of the health states defined. Hospitalizations tend to skew these averages but it has been observed that over a period of time the averages tend to "regress to a mean" value. Analysis must take into account these variations and adjust values accordingly.

This is, of course, the simplest static description of the population. If onset dates for the chronic disease and associated lab values of risk factors (lab data such as blood pressure, LDL, HDL, and HbA1 C, for example) were available then it would be possible to divide and classify each of the health states in our model in finer detail, such as "early stage", "normal stage" and "late stage". Currently such data are not readily available and so we do not include them in the analysis. Those skilled in the art will recognize that alternative formulations with this and other "fine structures" could be used that would preserve many aspects of the current invention.

Dynamic Component and Temporal evolution: Because chronic diseases offer no cure, with passage of time, patients either remain in the same health state or move to a more severe one to the right. (Remember that health states are ordered, left to right, in increasing order of severity. See FIG. 1.) Therefore, the time development of the patient population in this model is simply defined by the number of patient transitions from one health state to another (always to the right), and the associated cost increases that arise from the increasing severity of treatment in the new health state. (See FIG. 2) By way of the cost model this asserts an elegant way to lower future healthcare costs by instituting clinical processes to minimize patient transitions and using the number of transitions as a unique and specific (but inverse) measure of the efficiency of the clinical programs.

DETAILS OF THE INVENTION

The "one chronic disease" segment is explicitly split into independent sub-segments, according to each named chronic disease, such as "diabetes", "heart problems", "hyper-tension", "hyper cholesterol", "asthma", "obesity", "osteoarthritis" and "cancer". Depending on the patient population other chronic illness may need to be added. Cancer is not really a chronic condition but costs for treating cancer are so great that it tends to mask and overwhelm chronic treatment costs. Accordingly it seemed prudent for analytical purposes to separate cancer patients into their own category.

The "two chronic disease" category would include patients with two of the above listed chronic conditions; the "three chronic disease" would include patients with three of the above chronic illness and so on. Each chronic segment is also characterized by an "average" annual cost. Of course, these average costs will vary across the nation, but they are meaningful when viewed within a geographical region. Multiplying the number of patients in each category by the average annual costs would then yield the cost for treating patients within that health state of the population.

This cost model helps in defining the time evolution of the population, not just in terms of age but more in terms of patients transitioning from one population segment to another with higher severity, thus incurring the increased costs associated with treatment of higher severity chronic problems. Note that a chronic illness, by, definition, has no cure and so a patient's condition can never be reversed. Therefore, the progression of the population in this new cost model is also unidirectional, just like "time." (See FIG. 1) This has important consequences, simplifying calculations of future estimates of treatment costs for the patient population. FIG. 2 is an illustrative example showing the cost increases of almost $25 million for a sample population of about 55,000 non chronic patients in a one year period.

Currently preventive care is considered as an "add-on" service that needs to be justified on an ROI basis. The story doled out by disease management advocates is that every $1 spent will yield $3 in savings in the "long term". There is the rub. Mathematics needed to arrive at savings at the end of the long term is fraught with fuzzy assumptions designed by vendors to confirm the predicted savings. This approach has soured many employers and preventive care has less support than before.

Here again the new cost model has a built in advantage. As illustrated in the example in FIG. 2, when an additional $25 million is incurred because of patients acquiring chronic complications, preventive care becomes a crucial part of the service that is purchased. And its importance is directly measured by the lessening of patient transitions on a monthly basis. The cost savings are easy to calculate. No fuzzy math— just the facts.

In the last decade the concept of "population based medicine" has taken root. The central thrust of such a program is to reduce health disparity in a community by offering uniform treatment and support, especially for chronic patients, through physician office and community resources. While large health systems have tried to adopt such programs, patients receive "population based" treatments for, say their chronic condition, but for other medical services they go back to their conventional primary care doctors. In other words, the treatment receiving groups remain as discrete segments, with no relationship to the rest of the patients. In other words, it is a patchwork of services that is offered, with "population based medicine" offered in stand alone silos. Contrasted against this, this model is proposing a "chronic population based delivery system". In this model the entire population is divided according to chronic illness, and at any one time a patient is necessarily part of a population characterized by a disease state. These population segments are related because as transitions occur, patients migrate from one population segment to another. In this context what we are proposing can be viewed as a cost management program for "chronic population based delivery system".

Because this new cost model represents time evolution of a population group more accurately than the simple age based and statistical schemes in current use, it will complement the underwriting of insurance policies and community rating for self-insured organizations. A fifty year old chronic patient with a heart problem can incur a huge hospital cost after a stroke that can never be accurately captured in an "age based" underwriting model. In the future, actuaries will also be required to use chronic cost models lest they continue to underestimate total costs as they do now.

Here then are the highlights of this invention:

- This is a new cost model where patients are segmented into "health states" according to the various chronic illnesses and then further divided according to severity.
- The cost for treating patients in each of these segments is different, with higher costs being associated with an increasing severity of disease.
- Time evolution of the population then consists of patients making transitions from one disease segment (or health state) to a more severe one and thus incurring higher treatment costs in the process.
- The goal is to keep patients within their health states and minimize patient transitions. Preventive care programs are designed to accomplish this goal.
- The number of patient transitions in a month then becomes the new "metric" that defines healthcare costs. It's a quick (short term) measure of progress—both success and/or failure of a preventive care program. Corresponding to specific preventive care programs it is possible to define burden numbers that are counts of transitions of patients that correspond inversely to the success of a program.
- Financial managers can compare efficacy of preventive care programs by tracking the number of patient transitions each month from one disease group to another. Contrasted against this, current cost models yield measurable results only many years after the launch of programs.

One Embodiment of the Invention in a Computer Software:

HealthKeys is a Decision Support Software for CFOs of Companies & Healthplans

The principles enunciated in defining the new cost model has been incorporated in a computer software program to build a useful, tangible and concrete result. It is really the best mode of the invention but it can take many forms. It can be used to build a new epidemiological model, to create a supplemental underwriting tool especially for a "population", to forecast claim costs, to monitor health costs and track the effects of preventive care programs in population segments.

A new cost model could help employers who are on the sidelines become more active in the management of costs. A pure embodiment of the new cost model is in a decision support system (DSS) for a Chief Financial Officer (CFO) of a self-insured company, to help manage employee healthcare costs as he or she would manage any other cost center in their company. Of course, the same application could be used by healthplans as they manage healthcare delivery systems and track "performance" of provider groups. We prefer to illustrate the use of DSS in this application as used by self-insured companies because they are the ultimate purchasers of healthcare and empowering them is the best way to bring market-based reforms to the industry. The illustration could easily be modified to describe a healthplan and it falls within the true spirit and scope of the present invention HealthKeys is the tentative name assigned to this DSS. This will remain the working title until a name search and other inquiries clear it of legal hurdles in name selection.

Critical to understanding the cost model is the concept of patient transitions and the patient transition matrix elements. This is best explained in the context of an actual example, with precisely defined health states. For purposes of illustrating this embodiment of the new cost model we have chosen a sample of over 100,000 enrollees to be the totality of employee and dependent population, with about 30,000 of them with one or more chronic illness.

Implementation step 1: Static Component of the new model —Defining populations by grouping patients: Prior medical and pharma claims of the population must be analyzed to identify the top chronic diseases present. The disease type is based on the diagnosis codes in the medical claims. We considered only those diseases that cost at least 10% of the total as distinct disease types.

FIG. 3 is a sample flow chart illustrating the identification of patients with Diabetes.

Implementation Step 2: Monthly cost of treatment for each chronic state: The average cost for treatment in each disease state category was calculated using prior medical and pharma claims. A moving average based on the last three months of costs seemed to eliminate the peak effects from an unusual number of hospitalizations during a month. As pointed out earlier, with time there is a tendency of these averages to converge, and this phenomenon is referred to in the industry as a "regression to the mean." It is important to recognize that the "average cost" is influenced by such factors as the discounts obtained from providers, substitution of generics for brand name drugs, limiting access to specialists, expensive tests using referral management and managing cases to prevent unnecessary hospitalizations or visits to ERs. All of these are being handled in current delivery systems, some with more success than others. The point to note is that if these average costs rise then the counter-actions to be taken are well known.

Implementation Step 3: Dynamic and temporal component of population

In our new cost model increasing medical need is a natural consequence of a patient transitioning from one health status to a more complex one. Age is then not the real reason for increased cost—just poor health.

There is an important distinction between healthcare and other "cost centers" in a company. While other cost centers can be adjusted when a monthly cost exceeds budget, healthcare costs as defined here cannot be reversed, as they are costs of chronic diseases that are irreversible. In other words, once you incur these costs they become a recurring permanent and monthly cost as long as the employee remains with the company.

It is now possible to study the "time evolution" of a population, divided according to various health states. (See FIG. 4) The monthly total of patient transitions will give us an accurate reading of the efficacy of a preventive care program. An ideal that is impossible to reach would be to have zero patient transitions.

The following example will help illustrate this better. Table 1 shows what happened to a sample population in July 2007. The row "Cost" shows the monthly average cost for the various disease types, as given in the next row. Monthly cost for Non chronic patient is $165, for Heart patients $972, for Diabetes patients $472 and so on.

FIG. 4 depicts the flow diagram for patient transitions.

The matrix entries in FIG. 7 (see section on Drawings for the full matrix) are interpreted as follows. Consider Row 3 beginning with "NC"

The row beginning "NC" is saying that 883 non chronic patients acquired chronic diseases in July 2007, with 14 having "Heart" problems, 43 with Diabetes, 173 with cholesterol, 199 with hypertension and so on. If you add all the numbers of patients who transitioned then the total will be 883.

Consider next Row 4 (FIG. 7.) beginning with "H":

The next row "H" says that 10 patients with Heart acquired more chronic conditions and moved to a more severe disease state. 9 acquired one more chronic condition and one acquired two more chronic conditions.

Consider next Row 5 (FIG. 7) marked as "D":

The next row "D" says that 39 diabetes patients transitioned to more complex disease states: 31 with one more condition, 5 with 2 more conditions and 3 becoming cancer patients.

Consider Row 15 (FIG. 7) marked as "Net Change":

The last row is the "net change" in the number of patients in each disease state. In the case of "H", 14 new non chronic patients acquired heart but 10 with heart moved to other disease states, leaving a net increase of 4 patients in H.

Permanent Cost Impact of Transitions: Notice also that this matrix can help us calculate the incremental costs associated with each transition, by using the entries in the row called "Cost". For example, from Row 1 (FIG. 7) we deduce that 173 patients having cholesterol problems meant the cost for each of those patients rose from $165 to $284, a net increase of $119 per patient for 173 patients or a total monthly increase of $20,587 in medical costs. The point to keep in mind is that this single month's activity has added almost $250,000 to the annual cost —and because chronic patients have no cure, this becomes a permanent additional cost to the company.

Implementation Step 4: "What if?" analysis: A financially trained person can use the transition matrix given above to set goals to lower the number of transitions and thus the related costs. The goals must, of course, be clinically reasonable.

In the above matrix, we see (Row 3, Col. 10 in FIG. 7) that 98 non chronic patients acquired TWO chronic diseases in July. That seems a little unusual. Shouldn't their doctors have spotted one condition before it became worse and the second one manifested itself? It seems reasonable then to reduce this to say, 40, as a goal. Then 58 non chronic patients will not move to a "2D" state, and the monthly savings would then be $16,298. Other numbers can be adjusted similarly. HC & HT seem to have large numbers associated with them. Perhaps they can be lowered and the monthly savings can be calculated.

FIG. 5 is the flow chart that describes Implementation Step #4

Implementation Step 5: Clinical guidelines targeted to specific populations: Based on these new goals clinical experts will have to fashion a program that can help reduce transition to the new levels. So if the goal is to reduce the hypertensive population then the clinical program should be devised to identify patients with a tendency for high blood pressure and help them with a better exercise program and improved food habits to reduce that risk. So also, use of improved medication for those with high blood pressure can keep their condition from getting worse.

Depending on the transition matrix elements chosen for adjustment the clinical improvement program can be targeted to specific population segments. This is a vast improvement on current approaches when a "scatter shot" preventive program is instituted, with the hope that one or two may stick and produce desirable results.

Implementation Step 6: Did it work?: The success of the preventive care for a specific chronic disease is manifested in the decrease in patient transitions from and to the chronic disease state. Counting the change in patient population in any health state will be a measure of the success of a preventive care program. Month to month changes in the population will define the trend, and the goal would be to show a trend downwards, approaching zero transitions.

FIG. 6. describes the work flow associated with Implementation Step #6.

Roughly speaking there are two types of preventive care programs. "Primary preventive care program" is a program that targets people who don't have any chronic problems and the goal is to prevent such people from acquiring any chronic condition. "Secondary preventive care program" applies to the rest of the population, all of whom have at least one chronic problem. Loosely defined the secondary programs are designed to keep a chronic patient from getting worse i.e., preventing a person with a chronic condition from acquiring another new chronic condition. Associated with these two programs are two "burdens" that can be used to measure their success. Out of 10,000 non-chronic patients, the number of them acquire a chronic condition in a certain period (say, month or a quarter) could be defined as the "Primary Burden" for that chronic condition (for that period). Out of 10,000 patients with a chronic problem, the number of patients that acquire another chronic condition in a definite period could be defined as the "Secondary Burden" for that chronic condition. By normalizing the burden numbers to a population of 10,000 in this case it is easy to compare two care programs or interventions. Larger these numbers are, less effective are the corresponding programs. Of course this model also suggests other burden numbers, such as the number of patients who have two chronic conditions that acquire a third condition and so on. All of these variations fall within the spirit and scope of this invention.

It is possible to create a map of the region or the nation, characterized by the value of the burden numbers, to show the variation in the incidence, prevalence and severity of chronic conditions and their associated costs. FIG. 8 is a map of a state divided into arbitrary zones and with corresponding Primary and Secondary Burdens. This visual representation of a quantitative measure is very useful for studying trends in chronic diseases and their impact on public health.

Implementation Step 7: If there are too many transitions: If the goals are not accomplished then the clinical experts must try to understand why this is happening. It is possible to drill down on the claims data to identify the doctors who have the most patients involved in transitions and they could then be guided to follow improved treatment programs. Special educational programs as well as increased testing can be used to bring more patients into conformity with prevailing risk factor standards. It's the ingenuity of the clinical support staff that will eventually make the program a success. But it is the new cost model that will help measure the success and the savings.

While we have not provided the code for the software program, one skilled in the art could generate the necessary code based on the functions, the details of the transition matrix elements and the logic that has been disclosed. In particular, the 45 transition matrix elements defined in the above example can be defined in a straight forward, albeit inelegant, manner as a one dimensional vector with 45 elements.

When laboratory measurements become readily available it will be possible to associate patients according to the "severity" of a disease and thus model costs more accurately. It is not clear at this time if such data will be available for population groups and in its absence a proxy for severity could also be "onset date" of the disease. Even though medical claims data has a field to denote the onset of an event, currently it is used only in the context of pregnancies of women, to decide if it is a pre-existing condition or not.

It is possible to define other burden numbers considering new transitions and they can also be mapped. While one of the software embodiments of the present invention has been described in detail, it should be apparent that many modifications and variations to it are possible, all of which fall within the true spirit and scope of the present invention. This application is intended to cover those variations. It is intended that this application be limited only by those limitations in the above claims.

What is claimed is:

1. A non-transitory computer-readable medium storing computer-readable instructions that are executed by a processor to perform operations comprising:
   assigning an individual to a first health state from among a plurality of health states that are ordered based on a number of chronic diseases, wherein the number of chronic diseases is determined by parsing an insurance claim submitted by the individual and wherein one or more chronic diseases are identified based on one or more disease codes extracted from the insurance claim;
   upon determining an increase in the number of chronic diseases suffered by the individual, re-assigning the individual into a second health state from among the plurality of health states, the second health state being representative of an increase in the number of chronic diseases;
   determining a total number of transitions from the first health state into each of the plurality of health states, each transition the total number of transitions representing a number of individuals acquiring an increased number of chronic diseases; and
   representing each transition as an element in a transition matrix;
   using the transition matrix to determine a comparative efficacy of a preventative care program related to the number of changed chronic diseases, and
   using the transition matrix is to set a target for patient transition to implement an improved preventative care program.

2. The computer-readable medium of claim 1, wherein the first health state includes one of a zero-chronic disease state, a single-chronic disease state, a dual-chronic disease state, a triple-chronic-disease state, a multiple-chronic-disease state, or a cancerous state.

3. The computer-readable medium of claim 1, wherein the processor further performs operations including categorizing the individual based on a geographic region.

4. The computer-readable medium of claim 3, wherein the comparative efficacy of the preventative care program is isolated to the geographic region.

5. The computer-readable medium of claim 4, wherein the comparative efficacy of the preventative care program is isolated to a sub-set of a population within the geographic region.

6. The computer-readable medium of claim 4, wherein the comparative efficacy of the preventative care program is isolated to a first particular provider within the geographic region.

7. The computer-readable medium of claim 6, wherein the comparative efficacy of the preventative care program is compared with a second particular provider.

8. The computer-readable medium of claim 3, wherein the processor further performs operations including plotting the total number of individuals based on their respective geographic regions.

9. The computer-readable medium of claim 1, wherein the processor further performs operations including associating the total number of individuals transitioning into the second health state with a difference in a cost of treatment between the first health state and the second health state.

10. The computer-readable medium of claim 9, wherein the processor further performs operations including
    receiving the patient transition target via a user input; and
    associating the patient transition target with a cost saving to perform a "what if" analysis.

11. The computer-readable medium of claim 1, wherein each health state is a basis vector that uniquely describes a population.

12. A method, comprising:
    identifying, by a processor executing computer-readable instructions, a population suffering from a first number of chronic diseases;
    determining, by the processor, a number of individuals within the population that transition over time to a second number of chronic diseases, the second number being representative of an increased number of chronic diseases;
    representing, by the processor, a difference between the first number and the second number as an element of a transition matrix; and
    associating, by the processor, the difference with a comparative efficacy of a preventative care program;
    wherein the comparative efficacy is determined by comparing the transition matrix with a second transition matrix associated with a second preventative care program; and
    wherein the first and second numbers are determined by parsing one or more insurance claims submitted by individuals and wherein the one or more chronic diseases are identified based on one or more disease codes extracted from the insurance claims.

13. The method of claim 12, further comprising categorizing, by the processor, the number of individuals based on a geographic region.

14. The method of claim 13, further comprising isolating, by the processor, the comparative efficacy of the preventative care program to the geographic region.

15. The method of claim 14, further comprising isolating, by the processor, the comparative efficacy of the preventative care program to a sub-set of a population within the geographic region.

16. The method of claim 14, further comprising isolating, by the processor, the comparative efficacy of the preventative care program to a particular provider or group of providers within the geographic region.

17. A non-transitory computer-readable medium storing computer-readable instructions that are executed by a processor to perform operations comprising:
   assigning a plurality of individuals into a health state based solely on a number of chronic diseases suffered by each of the plurality of individuals, wherein the number of chronic diseases is determined by parsing one or more insurance claims submitted by an individual and wherein one or more chronic diseases are identified based on one or more disease codes extracted from the one or more insurance claims;
   determining a number of individuals among the plurality of individuals transitioning over time from said health state into one of a plurality of more complex health states, wherein each of the plurality of more complex health states represents an increased number of chronic diseases suffered by the number of individuals; and
   representing each transition from the health state into each of said plurality of more complex health states as an element in a transition matrix, with any changes in the transition matrix being associated with a preventative care program;
   using a comparison of the transition matrix with a second transition matrix with a second transition matrix associated with a second preventative care program to determine enables a comparative efficacy of the first and second preventative care programs.

\* \* \* \* \*